(12) United States Patent
Uhrich et al.

(10) Patent No.: US 8,263,060 B2
(45) Date of Patent: Sep. 11, 2012

(54) FAST DEGRADING POLYMERS

(75) Inventors: Kathryn E. Uhrich, Plainfield, NJ (US); Young Mi Kim, Seoul (KR)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 934 days.

(21) Appl. No.: 11/915,284

(22) PCT Filed: May 23, 2006

(86) PCT No.: PCT/US2006/019848
§ 371 (c)(1),
(2), (4) Date: Sep. 16, 2008

(87) PCT Pub. No.: WO2006/127667
PCT Pub. Date: Nov. 30, 2006

(65) Prior Publication Data
US 2009/0035248 A1 Feb. 5, 2009

Related U.S. Application Data

(60) Provisional application No. 60/683,831, filed on May 23, 2005.

(51) Int. Cl.
*A61K 31/74* (2006.01)
(52) U.S. Cl. .................................................. 424/78.08
(58) Field of Classification Search ........................ None
See application file for complete search history.

(56) References Cited

U.S. PATENT DOCUMENTS

| | | | |
|---|---|---|---|
| 6,468,519 B1 | 10/2002 | Uhrich | |
| 6,486,214 B1 | 11/2002 | Uhrich | |
| 6,602,915 B2 | 8/2003 | Uhrich | |
| 6,613,807 B2 | 9/2003 | Uhrich | |
| 6,685,928 B2 | 2/2004 | Uhrich et al. | |
| 6,689,350 B2 | 2/2004 | Uhrich | |
| 7,122,615 B1 | 10/2006 | Uhrich | |
| 7,396,527 B2 | 7/2008 | Uhrich | |
| 7,411,031 B2 | 8/2008 | Uhrich et al. | |
| 7,534,852 B2 | 5/2009 | Uhrich | |
| 7,662,864 B2 | 2/2010 | Kanamathareddy et al. | |
| 7,666,398 B2 | 2/2010 | Uhrich | |
| 7,985,415 B2 | 7/2011 | Giroux | |
| 8,017,714 B2 | 9/2011 | Uhrich | |
| 8,088,405 B2 | 1/2012 | Uhrich | |
| 2004/0038948 A1 | 2/2004 | Uhrich | |
| 2004/0096476 A1 | 5/2004 | Uhrich et al. | |
| 2005/0249697 A1 | 11/2005 | Uhrich et al. | |
| 2006/0013851 A1 | 1/2006 | Giroux | |
| 2006/0057179 A1 | 3/2006 | Giroux | |
| 2007/0098800 A1 | 5/2007 | Giroux et al. | |

(Continued)

FOREIGN PATENT DOCUMENTS

WO    WO 99/12990    3/1999

(Continued)

OTHER PUBLICATIONS

PCT International Search Report; International App. No. PCT/US06/19848; Sep. 29, 2006.

(Continued)

*Primary Examiner* — Paul Dickinson
(74) *Attorney, Agent, or Firm* — Viksnins Harris & Padys PLLP

(57) ABSTRACT

The invention provides polyanhydrides that degrade in less than 60 hours following topical administration to deliver biologically active compounds.

27 Claims, 4 Drawing Sheets

U.S. PATENT DOCUMENTS

| | | |
|---|---|---|
| 2007/0196417 A1 | 8/2007 | Uhrich |
| 2008/0226583 A1 | 9/2008 | Uhrich |
| 2008/0233078 A1 | 9/2008 | Uhrich |
| 2010/0152410 A1 | 6/2010 | East et al. |
| 2010/0272670 A1 | 10/2010 | Uhrich et al. |
| 2010/0291180 A1 | 11/2010 | Uhrich |
| 2010/0291181 A1 | 11/2010 | Uhrich et al. |
| 2010/0310498 A1 | 12/2010 | Kanamathareddy et al. |
| 2011/0022161 A1 | 1/2011 | Uhrich et al. |
| 2012/0058155 A1 | 3/2012 | Uhrich et al. |

FOREIGN PATENT DOCUMENTS

| | | |
|---|---|---|
| WO | WO 01/28492 | 4/2001 |
| WO | WO 01/41753 | 6/2001 |
| WO | WO 02/09767 | 2/2002 |
| WO | WO 02/09768 | 2/2002 |
| WO | WO 02/09769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2007/143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |

OTHER PUBLICATIONS

Brem, H. et al. "Placebo-controlled trial of safety and efficacy of intraoperative controlled delivery by biodegradable polymers of chemotherapy for recurrent gliomas", *The Lancet*, vol. 345, pp. 1008-1012, 1995.

Chafi, N. et al., "Dosage form with salicylic acid attached to a polyanhydride polymer dispersed in an Eudragit matrix", *International Journal of Pharmaceuticals*, vol. 52, pp. 203-211, 1989.

Goperfich, A., "Mechanisms of polymer degradation and erosion", *Biomaterials*, vol. 17, pp. 103-114, 1996.

Goperfich, A. et al., "Polyanhydride degradation and erosion", *Advanced Drug Delivery Reviews*, vol. 54, pp. 911-931, 2002.

Hanes, J. et al., "Degradation of porous poly(anhydride-*co*-imide microspheres and implications for controlled macromolecule delivery", *Biomaterials*, vol. 19, pp. 163-172, 1998.

Leong, K. W. et al., "Polyanhydrides for controlled release of bioactive agents", *Biomaterials*, vol. 7, pp. 364-371, 1986.

Quick, D. J., "Delivering DNA from photocrosslinked, surface eroding polyanhydrides", *Journal of Controlled Release*, vol. 97, pp. 333-343, 2004.

Sata, H. et al., "Study on antithrombogenicity of poly[β-(acetylsalicylyloxy)ethyl methacrylate relative to poly(hydroxyethyl methacrylate)", *J. of Biomater. Sci. Polymer Edn.*, vol. 2, pp. 1-13, 1991.

Tamada, J. A. et al., "Erosion kinetics of hydrolytically degradable polymers", *Proc. Natl. Acad. Sci. USA*, vol. 90, pp. 552-556, 1993.

Uhrich, K. E. et al., "Synthesis and Characterization of Degradable Poly(anhydride-*co*-imides)", *Macromolecules*, vol. 28, pp. 2184-2193, 1995.

Von Burkersroda, F. et al., "Why degradable polymers undergo surface erosion or bulk erosion", *Biomaterials*, vol. 23, pp. 4221-4231, 2002.

Whitaker-Brothers, K. et al., "Poly (anhydride-ester) fibers: role of copolymer composition on hydrolytic degradation and mechanical properties", *Journal of Biomedical Materials Research*, vol. 70A, pp. 309-318, 2004.

Anastasiou, T. J. et al., "Novel Polyanhydrides with Enhanced Thermal and Solubility Properties", *Macromolecules*, vol. 33, pp. 6217-6221, 2000.

Elvira, C. et al., "Complexation of polymeric drugs based on polyacrylic chains with aminosalicylic acid side groups", *Journal of Materials Science: Materials in Medicine*, vol. 8, pp. 743-746, 1997.

Elvira, C. et al., "Free radical copolymerization of methyl methacrylate with methacrylic monomers derived from salicylic acid. Microstructural analysis, chain flexibility and hydration behaviour of the prepared copolymers", *Polymer*, vol. 40, pp. 6911-6924, 1999.

Fan, J. et al., "The Effect of Substitution Levels on the Luminescent and Degradation Properties of Fluorescent Poly(ester-anhydride)s", *Journal of Applied Polymer Science*, vol. 100, pp. 1214-122, 2006.

Kricheldorf, H. R. et al., "Whisker 11. Poly(ester-amide)s derived from vanillic acid and 4-aminobenzoic acid", *Polymer*, vol. 36, pp. 1697-1705, 1995.

Langer, R., "Biomaterials in Drug Delivery and Tissue Engineering: One Laboratory's Experience", *Acc. Chem. Res.*, vol. 33, pp. 94-101, 2000.

Leong, K. W. et al., "Bioerodible polyanhydrides as drug-carrier matrices. II. Biocompatibility and chemical reactivity", *Journal of Biomedical Materials Research*, vol. 20, pp. 51-64, 1986.

Mathiowitz, E. et al., "Biologically erodable microspheres as potential oral drug delivery systems", *Nature*, vol. 386, pp. 410-414, 1997.

Nagata, M., "Synthesis, Characterization, and Hydrolytic Degradation of Copolyesters of 3-(4-Hydroxyphenyl) propionic Acid and *p*-Hydroxybenzoic Acid, Vanilic Acid, or Syringic Acid", *Journal of Applied Polymer Science*, vol. 78, pp. 2474-2481, 2000.

Prudencio, A. et al., "Effect of Linker Structure on Salicylic Acid-Derived Poly(anhydride-esters)", *Macromolecules*, vol. 38, pp. 6895-6901, 2005.

Rivas, B. L. et al., "Analysis of the interactions of biologically active poly(methacrylic-aminosalicylic acid) supports with $Ca^{2+}$ and $Zn^{2+}$ by ultrafiltration", *Journal of Membrane Science*, vol. 192, pp. 187-191, 2001.

Roman, J. S. et al., "Experimental studies of the antithrombogenic behaviour of Dacron vascular grafts coated with hydrophilic acrylic copolymers bearing salicylic acid residues", *Journal of Biomedical Materials Research*, vol. 32, pp. 19-27, 1996.

Sanders, A. J. et al., "Synthesis and Characterization of Polyanhydride Copolymers for Controlled Drug Delivery", *Polymer Preprints*, vol. 40, pp. 888-889, 1999.

Uhrich, K. E. et al., "In Vitro Degradation Characteristics of Poly(anhydride-imides) Containing Pyromellitylimidoalanine", *Journal of Polymer Science*, vol. 34, pp. 1261-1269, 1996.

Uhrich, K. E. et al., "Polymeric Systems for Controlled Drug Release", *Chem. Rev.*, vol. 99, pp. 3181-3198, 1999.

Chasin M. et al., "Biodegradable Polymers as Drug Delivery Systems", *Polyanhydrides as Drug Delivery Systems*, Ch. 2, pp. 43-70, 1990.

Woo, G.L.Y., et al., "Synthesis and characterization of a novel biodegradable antimicrobial polymer", *Biomaterials*, 21, 1235-1246, (2000).

FAST DEGRADING POLYMERS

PRIORITY OF INVENTION

This application is a National Stage application under 35 U.S.C. §371 and claims benefit under 35 U.S.C. §119(a) of International Application No. PCT/US2006/019848 having an International Filing Date of 23 May 2006, which claims priority from U.S. Provisional Application No. 60/683,831, filed 23 May 2005.

GOVERNMENT FUNDING

The invention described herein was made with government support under Grant Number DE 13207 awarded by the National Institutes of Health. The United States Government has certain rights in the invention.

BACKGROUND OF THE INVENTION

Biodegradable polyanhydrides have been extensively researched for use as biomaterials for tissue engineering and drug delivery. Most polyanhydrides are biodegradable and biocompatible polymers that undergo hydrolysis in vitro and in vivo to release water-soluble biocompatible degradation products. These polymers completely degrade due to the hydrolytically labile nature of the anhydride bonds and their degradation rate can be controlled by manipulating the polymer composition. Polyanhydrides are predominantly surface eroding, which allows a controlled release, thus avoiding a burst release that can cause non-desirable side effects. All of these features make polyanhydrides useful for delivering biologically active compounds. See Uhrich, K.; et al., *Macromolecules* 1995, 28, 2184-2193; Uhrich, K.; et al., *J. Polym. Sci., Polym. Chem. Ed.* 1996, 34, 1261-1269; Langer, R. *Acc. Chem. Res.* 2000, 33, 94-101; Anastasiou, T.; Uhrich, K. *Macromolecules* 2000, 33, 6217-6221; Mathiowitz, E., et al., *Nature* 1997, 386, 410-414; Chasin, M.; Langer, R. *Biodegradable polymers as drug delivery systems: New York,* 1990; Brem, H., et al., *Lancet* 1995, 345, 1008-1012; Hanes, J.; Chiba, M.; Langer, R. *Biomaterials* 1998, 19, 163-172; Leong, K, et al., *Biomaterials* 1986, 7, 364-371; Leong, K., et al., *J. Biomed. Mater. Res.* 1986, 20, 51-64; Sanders, A., et al., *Polym. Prepr.* 1999, 40, 888; Gopferich, A.; Tessmar, *J. Adv. Drug Del. Rev.* 2002, 54, 911-931; Gopferich, A. *Biomaterials* 1996, 17, 103-114; Whitaker-Brothers, K.; Uhrich, K. *J. Biomed. Mater. Res.* 2004, 70A, 309-318; Prudencio, A.; Schmeltzer, R. C.; Uhrich, K. E. *Macromolecules* 2005, 38, 6895-6901; Von Burkersroda, F.; Schedl, L.; Gopferich, A. *Biomaterials* 2002, 23, 4221-4231; Tamada, J.; Langer, R. *Proc. Natl. Acad. Sci. U.S.A.* 1993, 90, 552-556; and Quick, D.; and Macdonald, K.; Anseth, K. *J. Control. Rel.* 2004, 97, 333-343.

Previously, Erdmann et al. reported the synthesis of a poly (anhydride-ester) comprised of salicylic acid (SA) as a novel degradable biomaterial in which the drug, i.e. SA, is chemically incorporated into the polymer backbone and not attached as a side group or physically admixed. This unique system releases a high load of salicylic acid and sebacic acid upon hydrolysis of the ester and anhydride bonds in the backbone.

Phenolic compounds have been known for their wide biological activity, among which their antioxidant and antimicrobial activities stand out. Copolyesters containing natural non-toxic phenolic derivatives such as vanillic acid (VA) and syringic acid (SGA) were previously prepared and their mechanical properties studied (see Nagata, M., *J. Applied Polymer Sci.* 2000, 78, 2474-2481; Kricheldorf, H., et al., *Polymer* 1995, 36, 1697-1705; and Fan, J. et al., *J. Applied Polymer Sci.* 2006, 100, 1214-1221). However no study on the phenolic derivative release from these copolyesters was reported. See San Roman, J., et al., *J. Biomed. Mater. Res.* 1996, 32, 19-27; Sato, H., et al., *Biomater. Sci. Polymer. Ed.* 1991, 2, 1-13; Elvira, C., et al., *Polymer* 1999, 40, 6911-6924; Chafi, N.; Montheard, J.; Vergnaud, *J. Int J Pharm* 1989, 52, 203-211; Rivas, B., et al., *J. Membrane Sci.* 2001, 192, 187-191; and Elvira, C.; San Roman, J. *J. Mater. Sci.: Mater. in Med.* 1997, 8, 743-746.

In spite of the above disclosures, there remains a need for novel materials that can be applied to a wide range of applications. For example, there is a need for fast degrading polymers that can be used to deliver biologically active compounds via topical administration.

SUMMARY OF THE INVENTION

In one embodiment the invention provides a composition of the invention which is a composition suitable for topical administration to an animal comprising a polyanhydride having a backbone that degrades within 60 hours of administration to provide a biologically active compound.

In another embodiment the invention provides a composition suitable for topical administration to an animal that comprises microspheres that degrade within 60 hours of administration, the microspheres comprising a polyanhydride having a backbone that comprises a hydroxy aryl carboxylic acid.

In another embodiment the invention provides a method for promoting an antioxidant, anticeptic, or antibacterial effect in an animal comprising topically administering a composition of the invention to the animal.

A method for administering a biologically active compound to an animal comprising topically applying to the animal a composition that comprises a polyanhydride having a backbone that degrades within 60 hours of applying to provide the biologically active compound.

In another embodiment the invention provides a composition of the invention for use in medical therapy.

In another embodiment the invention provides the use of a composition of the invention to prepare a medicament for promoting an antioxidant, anticeptic, or antibacterial effect when administered to an animal (e.g. a mammal).

In another embodiment the invention provides a polyanhydride that comprises units of the following formula (I):

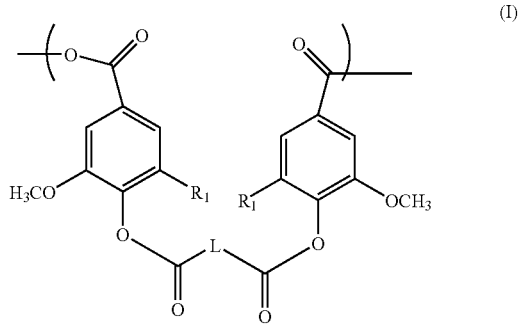

wherein:
each $R_1$ is independently H, or methoxy; and
L is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of $(C_1\text{-}C_6)$alkoxy, $(C_3\text{-}C_6)$cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$allylthio, azido, cyano, nitro, halo, hydroxy, oxo, carboxy, aryl, aryloxy, heteroaryl, and heteroaryloxy. In one specific embodiment of the invention the polyanhydride has a backbone that comprises repeating units of formula (I).

In another embodiment the invention provides a method for preparing a polyanhydride of formula (I):

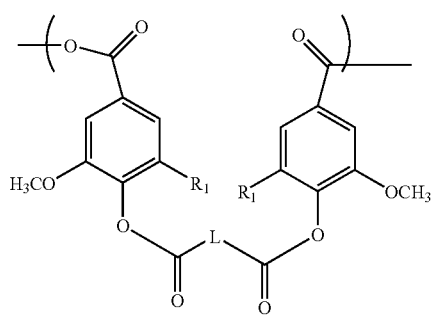

(I)

comprising polymerizing a corresponding compound of formula (II):

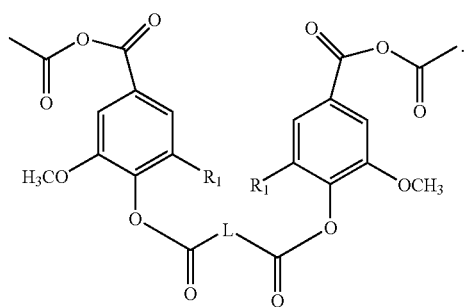

(II)

In another embodiment the invention provides a method for preparing a compound of formula (II) comprising acylating a corresponding diacid of formula (III):

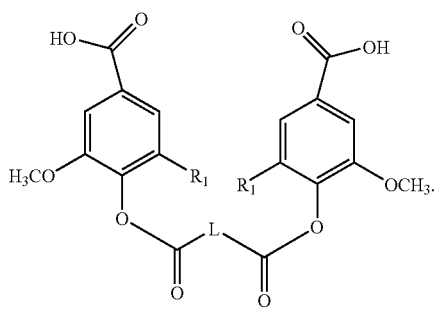

(III)

In another embodiment the invention provides a compound of formula (III):

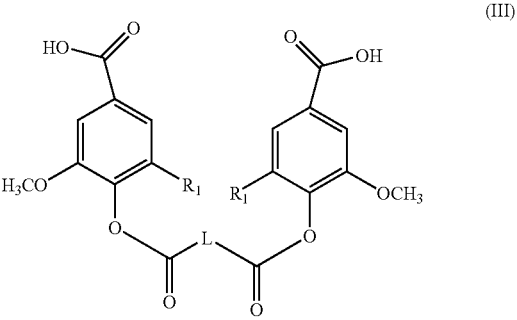

(III)

wherein:
each $R_1$ is independently H, or methoxy; and
L is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of $(C_1\text{-}C_6)$alkoxy, $(C_3\text{-}C_6)$cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$alkylthio, azido, cyano, nitro, halo, hydroxy, oxo, carboxy, aryl, aryloxy, heteroaryl, and heteroaryloxy; or a pharmaceutically acceptable salt thereof.

In another embodiment the invention provides a method for promoting an antioxidant, anticeptic, or antibacterial effect comprising topically administering a compound of formula (III) or a pharmaceutically acceptable salt thereof to an animal (e.g. mammal).

In another embodiment the invention provides a compound of formula (III) or a pharmaceutically acceptable salt thereof for use in medical therapy.

In another embodiment the invention provides the use of a compound of formula (III) or a pharmaceutically acceptable salt thereof to prepare a medicament for promoting an antioxidant, anticeptic, or antibacterial effect when administered to a mammal.

The invention also provides processes and intermediated disclosed herein that are useful for preparing polyanhydrides of formula (I).

DETAILED DESCRIPTION

Figure 3:
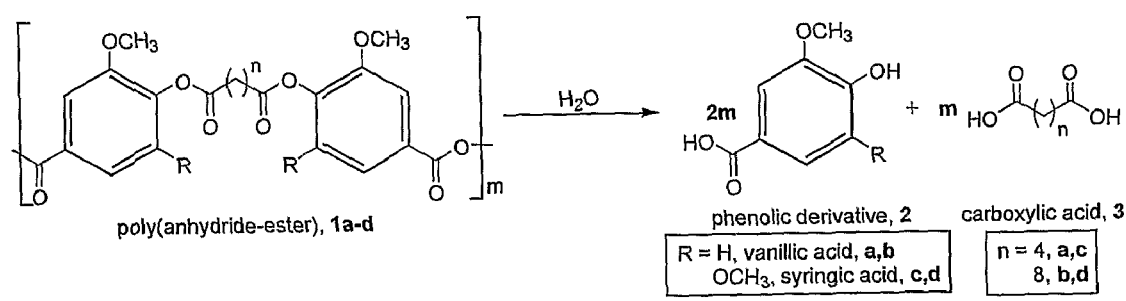
FIG. 3. Illustrates hydrolytic degradation of phenolic derivative-based poly(anhydride-esters), 1.

The synthesis of several poly(anhydride-esters) based on natural non-toxic aromatic hydroxy acids such as vanillic acid (VA) and syringic acid (SGA) with a high load of biologically active molecules in the polymer (from 67% up to 78% by weight) is described below. In addition, the degradation of the polymers (1) incorporating vanillic and syringic acid degraded into the phenolic hydroxy acid (2) and as well the carboxylic acid linker (3) (FIG. 3) is described.

The relationship between the methoxy substitution on the aromatic ring and polymer composition, and the physical properties of the corresponding polymer were assessed with respect to delivery of the biologically active compounds. In vitro degradation studies were performed. Cytotoxicity and bacterial inhibition assays were conducted to assess potential application as an antibacterial polymeric materials. Thus, the degradation of these polymers and their cytotoxicity has been evaluated.

Specific values identified herein for radicals, substituents, and ranges, are for illustration only; they do not exclude other defined values or other values within defined ranges for the radicals and substituents Degradation The invention provides compositions that comprise polyanhydrides that degrade rapidly following administration to deliver one or more biologically active compounds. In one embodiment of the invention, the polyanhydride degrades within 60 hours of administration. The term "degrades" as used generally herein means that at least 60% of the anhydride bonds in the backbone of the polymer have hydrolyzed in the stated time period. In one specific embodiment of the invention, at least about 75% anhydride bonds in the backbone of the polymer have hydrolyzed in the stated time period. In another specific embodiment of the invention, at least about 90% anhydride bonds in the backbone of the polymer have hydrolyzed in the stated time period. In another specific embodiment of the invention, at least about 98% anhydride bonds in the backbone of the polymer have hydrolyzed in the stated time period. In another specific embodiment of the invention, all the anhydride bonds in the backbone of the polymer have hydrolyzed in the stated time period.

The degradation rate for the polymers can be increased by incorporating electron donating groups into aromatic rings in the polymer backbone and by providing the polymers in the form of microspheres, which have a high surface area and thus allow for increased surface erosion.

Polymers of the Invention

The biocompatible, biodegradable polyanhydrides of the invention are useful in a variety of applications where delivery of a biologically active compound is desired. Examples of such applications include, but are not limited to, medical, dental and cosmetic uses. The fast degrading polymers are particularly useful for delivering biologically active compounds by topical administration.

The polymers of the invention may be prepared in accordance with methods commonly employed in the field of synthetic polymers to produce a variety of useful products with valuable physical and chemical properties. The polymers can be readily processed into pastes, films, coatings, microspheres and fibers, and may also be processed by compression molding and extrusion.

Polymers of the present invention can also be incorporated into oral formulations and into products such as skin moisturizers, cleansers, pads, plasters, lotions, creams, gels, ointments, solutions, shampoos, tanning products and lipsticks for topical application.

Preferably, the polymers of the invention comprise backbones wherein biologically active compounds and linker groups (L) are bonded together through ester linkages, thioester linkages, amide linkages, or a mixture thereof. Due to the presence of the ester, thioester, and/or amide linkages, the polymers can be hydrolyzed under physiological conditions to provide the biologically active compounds. Thus, the polymers of the invention can be particularly useful as a controlled release source for a biologically active compound, or as a medium for the localized delivery of a biologically active compound to a selected site.

The polyanhydrides can be prepared by the method described in Conix, Macromol. Synth., 2, 95-99 (1996) and by the methods described in International Patent Application Publication Number WO 02/009767. For example, a dicarboxylic acid can be acetylated in an excess of acetic anhydride at reflux temperatures followed by melt condensation of the resulting carboxylic acid anhydride at 180° C. for 2-3 hours to provide the polyanhydride polymers. The polymers can be isolated by precipitation into a suitable solvent (e.g. diethylether from methylene chloride). Useful polyanhydrides include both homopolymers and mixed polymers.

Polyanhydrides of the present invention typically have average molecular weights ranging between about 1500 daltons up to about 90,000 daltons, calculated by Gel Permeation Chromatography (GPC) relative to narrow molecular weight polystyrene standards. Some aromatic polyanhydrides have average molecular weights of about 1500 daltons, up to about 30,000 daltons calculated by Gel Permeation Chromatography (GPC) relative to narrow molecular weight polystyrene standards. Other aromatic polyanhydrides have average molecular weights of about 3000 daltons, up to about 25,000 daltons.

Microspheres

Polymer microspheres can be fabricated by a solvent evaporation technique using an oil/water emulsion (Yeagy, B. et al., *J. Microencapsulation* 2006, accepted). For example, the polymer is dissolved in methylene chloride (10% wt/vol or 0.1 g in 1 mL) and added dropwise to (a 40-fold excess or 40 mL) homogenized solution of 1% wt/vol poly(vinyl alcohol), and the aqueous and organic phases are emulsified by homogenization (PowerGen 700, Fisher Scientific, Pittsburgh, Pa.) for 2 minutes at a speed setting of 5. The emulsified solution is then stirred at room temperature to evaporate the organic solvent. The polymer precipitates as the methylene chloride evaporates, and the hardened microspheres are vacuum filtered, washed several times (by centrifugation and resuspension) with deionized water and freeze dried (Freeze Dry System/Freezone 4.5, Labconco, Kansas City, Mo.).

Therapies

The polyanhydrides are designed to degrade quickly to allow for delivery of biologically active compounds over a period of hours to a few days. Accordingly, in one embodiment of the invention, a biologically active compound can be dispersed in the matrix of the polymer, and can be released upon degradation of the polymer. In another embodiment of the invention, a biologically active compound can be appended to a polymer of the invention (i.e. not in the backbone of the polymer) with bonds that hydrolyze to release the biologically active compound under predetermined conditions. In another embodiment of the invention, the polymer backbone itself includes groups that provide one or more biologically active compounds upon degradation (e.g. hydrolysis) of the backbone. Combinations of the above embodiments of the invention are also possible. For example, the polymer backbone itself may include groups that provide one or more biologically active compounds upon degradation (e.g. hydrolysis) of the backbone, and there may also be biologically active compounds appended to the polymer backbone or dispersed in the matrix of the polymer.

Combination Therapies

The invention also provides compositions and methods that are useful for delivering two or more biologically active compounds. For example, in one embodiment of the invention, two or more biologically active compounds are dispersed within the polymer matrix, and can be released upon degradation of the polymer. In another embodiment of the invention, the polymer backbone itself includes groups that provide two or more biologically active compounds upon degradation (e.g. hydrolysis) of the backbone. Combinations of the above embodiments of the invention are also possible. For example, the polymer backbone itself may include groups that provide one or more biologically active compounds upon degradation (e.g. hydrolysis) of the backbone and there may also be other biologically active compounds dispersed in the matrix of the polymer. Alternatively, two polymers of the invention, each with a different biologically active compound in the backbone, can be administered together in a single composition.

Biologically Active Compounds

The term "biologically active compound" includes agents that provide a therapeutically desirable effect when administered to an animal (e.g., a mammal, such as a human). Therapeutic agents that can be included in the compositions described herein include analgesics, anesthetics, anti-Parkinson's agents, anti-infectives, antiacne agents, antibiotics, anticholinergics, anticoagulants, anticonvulsants, antidiabetic agents, antidyskinetics, antifibrotic agents, antifibrotics, antifungal agents, antiglaucoma agents, anti-inflammatory agents, antioxidants, antineoplastics, antiosteoporotics, antipagetics, antisporatics, antipyretics, antiseptics/disinfectants, antithrombotics, bone resorption inhibitors, calcium regulators, cardioprotective agents, cardiovascular agents, central nervous system stimulants, cholinesterase inhibitors, contraceptives, deodorants, dopamine receptor agonists, erectile dysfunction agents, fertility agents, gastrointestinal agents, gout agents, hormones, hypnotics, immunomodulators, immunosuppressives, keratolytics, migraine agents, motion sickness agents, muscle relaxants, nucleoside analogs, obesity agents, ophthalmic agents, osteoporosis agents, parasympatholytics, parasympathomimetics, prostaglandins, psychotherapeutic agents, respiratory agents, sclerosing agents, sedatives, skin and mucous membrane agents, smoking cessation agents, sympatholytics, synthetic antibacterial agents, ultraviolet screening agents, urinary tract agents, vaginal agents, and vasodilators (see Physicians' Desk Reference, 55 ed., 2001, Medical Economics Company, Inc., Montvale, N.J., pages 201-202).

The biologically active compounds can also comprise functional groups (including hydroxy groups, mercapto groups, amine groups, and carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer). Lists of therapeutic agents can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J. One skilled in the art can readily select therapeutic agents that possess the necessary functional groups for incorporation into the polymers of the invention from these lists.

Examples of anti-bacterial compounds suitable for use in the present invention include, but are not limited to, 4-sulfanilamidosalicylic acid, acediasulfone, amfenac, amoxicillin, ampicillin, apalcillin, apicycline, aspoxicillin, aztreonam, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, enoxacin, epicillin, flomoxef, grepafloxacin, hetacillin, imipenem, lomefloxacin, lymecycline, meropenem, moxalactam, mupirocin, nadifloxacin, norfloxacin, panipenem, pazufloxacin, penicillin N, pipemidic acid, quinacillin, ritipenem, salazosulfadimidine, sparfloxacin, succisulfone, sulfachrysoidine, sulfaloxic acid, teicoplanin, temafloxacin, temocillin, ticarcillin, tigemonam, tosufloxacin, trovafloxacin, vancomycin, and the like.

Examples of anti-fungal compounds suitable for use in the present invention include, but are not limited to amphotericin B, azaserine, candicidin(s), lucensomycin, natamycin, nystatin, and the like.

Examples of anti-neoplastic compounds suitable for use in the present invention include, but are not limited to 6-diazo-5-oxo-L-norleucine, azaserine, carzinophillin A, denopterin, edatrexate, eflornithine, melphalan, methotrexate, mycophenolic acid, podophyllinic acid 2-ethylhydrazide, pteropterin, streptonigrin, Tomudex® (N-((5-(((1,4-Dihydro-2-methyl-4-oxo-6-quinazolinyl)methyl)methylamino)-2-thienyl)carbonyl)-L-glutamic acid), ubenimex, and the like.

Examples of anti-thrombotic compounds for use in the present invention include, but are not limited to, argatroban, iloprost, lamifiban, taprostene, tirofiban and the like.

Examples of immunosuppressive compounds suitable for use in the present invention include, but are not limited to bucillamine, mycophenolic acid, procodazole, romurtide, ubenimex and the like.

Examples of NSAID compounds suitable for use in the present invention include, but are not limited to 3-amino-4-hydroxybutyric acid, aceclofenac, alminoprofen, bromfenac, bumadizon, carprofen, diclofenac, diflunisal, enfenamic acid, etodolac, fendosal, flufenamic acid, gentisic acid, meclofenamic acid, mefenamic acid, mesalamine, niflumic acid, olsalazine oxaceprol, S-adenosylmethionine, salicylic acid, salsalate, sulfasalazine, tolfenamic acid, and the like.

Examples of anti-oxidant compounds suitable for use in the present invention include, vanillic acid, syringic acid, p-coumaric acid, caffeic acid, gallic acid, ferulic acid, sinapic acid, protocatechuic acid, and p-hydroxybenzoic acid.

Biologically active compounds that can be incorporated into the backbone of degradable polymers as described herein typically have molecular weights of approximately 1,000 daltons or less. Additionally, if the biologically active compound is to be incorporated into the backbone of the polyanhydride, it must contain within its molecular structure one carboxylic acid group and at least one other functional group selected from carboxylic acid (—COOH), amine (—NHR), thiol (—SH), alcohol (—OH) or phenol (-Ph-OH).

A specific biologically active compound is 3-amino-4-hydroxybutyric acid, 6-diazo-5-oxo-L-norleucine, aceclofenac, acediasulfone, alminoprofen, amfenac, amoxicillin, amphotericin B, ampicillin, apalcillin, apicycline, aspoxicillin, azaserine, aztreonam, bambermycin(s), biapenem, bromfenac, bucillamine, bumadizon, candicidin(s), carbenicillin, carprofen, carumonam, carzinophillin A, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, denopterin, diclofenac, edatrexate, eflornithine, enfenamic acid, enoxacin, epicillin, etodolac, flomoxef, flufenamic acid, grepafloxacin, hetacillin, imipenem, lomefloxacin, lucensomycin, lymecycline, meclofenamic acid, mefenamic acid, melphalan, meropenem, methotrexate, moxalactam, mupirocin, mycophenolic acid, mycophenolic acid, nadifloxacin, natamycin, niflumic acid, norfloxacin, nystatin, oxaceprol, panipenem, pazufloxacin, penicillin N, pipemidic acid, podophyllinic acid 2-ethylhydrazide, procodazole, pteropterin, quinacillin, ritipenem, romurtide, S-adenosylmethionine, salazosulfadimidine, sparfloxacin, streptonigrin, succisulfone, sulfachrysoidine, sulfaloxic acid, teicoplanin, temafloxacin, temocillin, ticarcillin, tigemonam, tolfenamic acid, Tomudex® (N-((5-(((1, 4-Dihydro-2-methyl-4-oxo-6-quinazolinyl)methyl)methylamino)-2-thienyl)carbonyl)-L-glutamic acid), tosufloxacin, trovafloxacin, ubenimex or vancomycin.

Linking Group "L"

The nature of the linking group "L" in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

A specific value for L is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

Another specific value for L is a divalent, branched or unbranched, saturated or unsaturated, hydrocarbon chain, having from 1 to 20 carbon atoms, wherein one or more (e.g. 1, 2, 3, or 4) of the carbon atoms is optionally replaced by (—O—) or (—NR—).

A more specific value for L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of ($C_1$-$C_6$) alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

Another more specific value for L is a divalent or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

Another more specific value for L is a divalent, branched or unbranched, saturated or unsaturated, hydrocarbon chain, having from 3 to 15 carbon atoms.

Another more specific value for $R^2$ is a divalent, branched or unbranched, hydrocarbon chain, having from 3 to 15 carbon atoms.

Another more specific value for L is a divalent, branched or unbranched, hydrocarbon chain, having from 6 to 10 carbon atoms.

Another more specific value for L is a divalent hydrocarbon chain having 7, 8, or 9 carbon atoms.

Another more specific value for L is a divalent hydrocarbon chain having 8 carbon atoms.

Another more specific value for L is a divalent, branched or unbranched, hydrocarbon chain, having from 4 to 8 carbon atoms.

Another more specific value for L is —$CH_2CH_2CH_2CH_2$—.

The compositions of the invention can be incorporated into a variety of products that can be used to topically deliver biologically active compounds. For example, the compositions of the invention can be incorporated into deodorants, baby care products (e.g. diapers and wipes), cosmetics, feminine hygene products, hair care products (e.g. shampoos, and conditioners), household cleaners (e.g. soaps and wipes) laundry products and fabric care products (e.g. soaps, fabric softeners) paper products (e.g. wipes), personal cleansing products (e.g. soaps) and skin care products (e.g. moisturizers).

For topical administration, it will generally be desirable to administer the polymers to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Useful dosages of the biologically active compound I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of biologically active compound in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The invention will now be illustrated by the following non-limiting Examples.

EXAMPLES

Example 1

Materials and Methods. Tetrahydrofuran (THF), pyridine, acetic anhydride, methylene chloride, and diethyl ether were purchased from Fisher (Fair Lawn, N.J.). All other fine chemicals and solvents were obtained from Aldrich (Milwaukee, Wis.) and used as received.

Proton nuclear magnetic resonance ($^1$H NMR) spectra were recorded on a Varian 300 MHz spectrometer. The samples (5-10 mg) were dissolved in a deuterated solvent (DMSO-$d_6$), which was also used as the internal reference. Infrared (IR) spectra were measured on a Thermo Nicolet/Avatar 360 FT IR spectrometer, by depositing samples onto NaCl plates (if liquid) or solvent-casting samples from methylene chloride onto NaCl plates (if solid).

Weight-averaged molecular weights (Mw) were determined by gel permeation chromatography (GPC) on a Perkin-Elmer liquid chromatography system consisting of a Series 200 refractive index detector, a Series 200 LC pump, and an ISS 200 advanced sample processor. A Dell OptiPlex GX110 computer running Perkin-Elmer TurboChrom 4 software was used for data collection and processing, and to automate the analysis via Perkin-Elmer Nelson 900 Series Interface and 600 Series Link. Polymers were dissolved in methylene chloride (5 mg/mL) and filtered through 0.45 µm poly(tetrafluoroethylene) (PTFE) syringe filters (Whatman, Clifton, N.J.) before elution. Samples were resolved on a Jordi divinylbenzene mixed-bed GPC column (7.8×300 mm) (Alltech Associates, Deerfield, Ill.) at 25° C., with methylene chloride as eluent at a flow rate of 0.5 mL/min. Molecular weights were calibrated relative to narrow molecular weight polystyrene standards (Polysciences, Dorval, Canada).

Thermal analyses were performed on a Perkin-Elmer system consisting of Pyris 1 DSC and TGA 7 analyzers with TAC 7/DX instrument controllers. Perkin-Elmer Pyris software was used for data collection on a Dell OptiPlex GX110 computer. For DSC, samples (5 mg) were heated under dry nitrogen gas. Data were collected at heating and cooling rates of 10° C./min with a two-cycle minimum. Glass transition temperatures were calculated as half Cp extrapolated. For TGA, samples (10 mg) were heated under dry nitrogen gas. Data were collected at a heating rate of 10° C./min. Decomposition temperatures were defined as the onset of decomposition.

Elemental analyses were provided by QTI (Whitehouse, N.J.). Melting points below 200° C. were obtained with a Mel-Temp apparatus at a heating rate of 1° C. per minute, while those above 200° C. were determined on the Pyris 1 DSC (see above).

Sessile-drop contact angles of phosphate buffer solution on polymer disks were measured using an automated Ramé-hart goniometer (Model 250, Netcong, N.J.) with DROPimage Advanced software. Angles were measured on 3 different disks for each polymer and an averaged value was taken. Polymers (150 mg) disks were prepared by pressing ground polymers (~150±5 mg) into 13 mm diameter×1 mm thick disks in an IR pellet die (International Crystal Laboratories, Garfield, N.J.) with a bench-top hydraulic press (Carver model M, Wabash, Ind. by applying a pressure of 5000 psi for 5 min.

Vanillic acid (VA) and syringic acid (SGA) concentrations in the degradation media were determined on a Perkin-Elmer HPLC system consisting of a 785A absorbance detector (Applied Biosystems, Foster City, Calif.), a Series 200 quaternary LC pump, and an ISS 200 autosampler. A Dell OptiPlex GX110 computer running Perkin-Elmer TurboChrom 4 software was used for data collection and processing, and to automate the analysis via Perkin-Elmer Nelson 900 Series Interface and 600 Series Link. Degradation media was filtered through 0.45 µm poly(tetrafluoroethylene) (PTFE) syringe filters (Whatman, Clifton, N.J.) before elution. Samples were resolved on a Zorbax C-8 reverse-phase column (4.6×150 mm) (Agilent, Foster City, Calif.) at 25° C. using a mixture of methanol:DDW:TFA 50:49.05:0.05 v/v/v as eluent at a flow rate of 1.0 mL/min to determine VA with UV detection at 251 nm and SGA with UV detection at 261 nm.

Poly(anhydride-esters) Precursors: Diacid Synthesis (5). Diacids were prepared by reaction of vanillic acid (2a) or syringic acid (2b) with the appropriate acyl chloride in the presence of a base (pyridine). The preparation of 5a is provided as an example. Vanillic acid (2a) (3.6 g, 21 mmol) was dissolved in THF (40 mL) and pyridine (5.2 mL, 64 mmol). Adipoyl chloride (4a) (1.6 mL, 11 mmol) dissolved in tetrahydrofuran (10 mL) was added dropwise over 5 minutes to the stirring reaction mixture at room temperature to afford a suspension. The reaction was stirred for 2 h at room temperature, poured over water (400 mL) and acidified to pH~2 using concentrated hydrochloric acid while stirring. The off-white solid (diacid, 5a) that formed was isolated by vacuum filtration, washed with water (3×100 mL) and dried overnight under vacuum at room temperature.

1,6-bis(3-methoxy-1,4-carboxyphenoxy)-hexanoate (5a). Yield: 73% (white powder). $^1$H NMR (DMSO-$d_6$): δ 7.60 (m, 4H, ArH), 7.20 (d, 2H, ArH), 3.80 (s, 6H, $CH_3$), 2.65 (t, 4H, $CH_2$), 1.75 (t, 4H, $CH_2$). IR (NaCl, $cm^{-1}$): 3600-3100 (OH, COOH), 1750 (C=O, ester), 1685 (C=O, COOH). Anal. Calcd.: C, 59.2%; H, 5.0%; O, 35.8%. Found: C, 58.8%; H, 4.9%; O, 36.3%; mp: 205-206° C.

1,10-bis(3-methoxy-1,4-carboxyphenoxy)-decanoate (5b). Yield: 77% (white powder). $^1$H NMR (DMSO-$d_6$): δ 7.60 (m, 4H, ArH), 7.20 (d, 2H, ArH), 3.80 (s, 6H, $CH_3$), 2.60 (t, 4H, $CH_2$), 1.65 (m, 4H, $CH_2$), 1.40 (m, 8H, $CH_2$). IR (NaCl, $cm^{-1}$): 3650-3100 (OH, COOH), 1760 (C=O, ester), 1695 (C=O, COOH). Anal. Calcd.: C, 62.2%; H, 6.0%; O, 31.8%. Found: C, 61.8%; H, 6.1%; O, 32.1%; mp: 176-178° C.

1,6-bis(3,5-dimethoxy-1,4-carboxyphenoxy)-hexanoate (5c). Yield: 70% (white powder). $^1$H NMR (DMSO-$d_6$): δ 7.25 (s, 4H, ArH), 3.80 (s, 12H, $CH_3$), 2.65 (t, 4H, $CH_2$), 1.75 (t, 4H, $CH_2$). IR (NaCl, $cm^{-1}$): 3650-3100 (OH, COOH), 1760 (C=O, ester), 1680 (C=O, COOH). Anal. Calcd.: C, 56.9%; H, 5.2%; O, 37.9%. Found: C, 56.6%; H, 5.1%; O, 38.3%; mp: 227-230° C.

1,10-bis(3,5-dimethoxy-1,4-carboxyphenoxy)-decanoate (5d). Yield: 79% (white powder). $^1$H NMR (DMSO-d$_6$): δ 7.25 (s, 4H, ArH), 3.80 (s, 12H, CH$_3$), 2.55 (t, 4H, CH$_2$), 1.65 (m, 4H, CH$_2$), 1.35 (m, 8H, CH$_2$). IR (NaCl, cm$^{-1}$): 3600-3100 (OH, COOH), 1765 (C=O, ester), 1695 (C=O, COOH). Anal. Calcd.: C, 59.8%; H, 6.1%; O, 34.1%. Found: C, 59.5%; H, 6.2%; O, 34.3%; mp: 193-195° C.

Monomer Synthesis (6). The diacid (5) (3.0 g) was activated with stirring in an excess of acetic anhydride (50 mL) at room temperature until the initial suspension becomes a clear solution (approximately 3-12 h). The excess acetic anhydride is removed by rotoevaporation at room temperature under vacuum to afford the monomer.

1,6-bis(3-methoxy-1,4-carboxyphenoxy)-hexanoate Monomer (6a). Yield: quantitative (orangish oil). $^1$H NMR (DMSO-d$_6$): δ 7.60 (m, 4H, ArH), 7.20 (d, 2H, ArH), 3.80 (s, 6H, CH$_3$), 2.65 (t, 4H, CH$_2$), 2.10 (s, 6H, CH$_3$), 1.75 (t, 4H, CH$_2$). IR (NaCl, cm$^{-1}$): 1810, 1735 (C=O, anhydride), 1760 (C=O, ester). T$_d$=274° C.

1,10-bis(3-methoxy-1,4-carboxyphenoxy)-decanoate Monomer (6b). Yield: quantitative (orangish oil). $^1$H NMR (DMSO-d$_6$): δ 7.60 (m, 4H, ArH), 7.20 (d, 2H, ArH), 3.80 (s, 6H, CH$_3$), 2.65 (t, 4H, CH$_2$), 2.10 (s, 6H, CH$_3$), 1.65 (m, 4H, CH$_2$), 1.35 (m, 8H, CH$_2$). IR (NaCl, cm$^{-1}$): 1820, 1735 (C=O, anhydride), 1770 (C=O, ester). T$_d$=348° C.

1,6-bis(3,5-dimethoxy-1,4-carboxyphenoxy)-hexanoate Monomer (6c). Yield: quantitative (white powder). $^1$H NMR (DMSO-d$_6$): δ 7.35 (s, 4H, ArH), 3.85 (s, 12H, CH$_3$), 2.70 (t, 4H, CH$_2$), 2.20 (s, 6H, CH$_3$), 1.80 (t, 4H, CH$_2$). IR (NaCl, cm$^{-1}$): 1810, 1720 (C=O, anhydride), 1765 (C=O, ester). T$_d$=290° C.

1,10-bis(3,5-dimethoxy-1,4-carboxyphenoxy)-decanoate Monomer (6d). Yield: quantitative (white powder). $^1$H NMR (DMSO-d$_6$): δ 7.30 (s, 4H, ArH), 3.80 (s, 12H, CH$_3$), 2.55 (t, 4H, CH$_2$), 2.20 (s, 6H, CH$_3$), 1.65 (m, 4H, CH$_2$), 1.35 (m, 8H, CH$_2$). IR (NaCl, cm$^{-1}$): 1810, 1725 (C=O, anhydride), 1765 (C=O, ester). T$_d$=351° C.

Polymer Synthesis (1). Monomer (6) (3.0 g) was placed in a 100 mL two-necked round-bottom flask with 24/40 joints with a vacuum joint in one neck and a Teflon vacuum-stirring adapter in the other. The reaction flask was heated up to 160° C. using a temperature controller (Cole Parmer) in a silicone oil bath under high vacuum (<2 mm Hg). During this time, the melt was actively stirred at ~100 rpm by an overhead stirrer (T-line Laboratory Stirrer, Talboys Engineering, Montrose, Pa.). Polymerization was complete when the viscosity of the melt remained constant and/or solidified (4 h). The polymer was cooled to room temperature, and isolated by precipitation in methylene chloride/diethyl ether (5 mL/100 mL).

Poly[1,6-bis(3-methoxy-1,4-carboxyphenoxy)-hexanoate] (1a). Yield: quantitative (off-white solid). $^1$H NMR (DMSO-d$_6$): δ 7.80 (m, 4H, ArH), 7.35 (d, 2H, ArH), 3.85 (s, 6H, CH$_3$), 2.70 (t, 4H, CH$_2$), 1.75 (t, 4H, CH$_2$). IR (NaCl, cm$^{-1}$): 1790, 1720 (C=O, anhydride), 1765 (C=O, ester). M$_w$=63100, PDI=1.3. T$_d$=268° C., T$_g$=59° C. Contact Angle: 60°.

Poly[1,10-bis(3-methoxy-1,4-carboxyphenoxy)-decanoate] (1b). Yield: quantitative (off-white solid). $^1$H NMR (DMSO-d$_6$): δ 7.75 (m, 4H, ArH), 7.30 (d, 2H, ArH), 3.85 (s, 6H, CH$_3$), 2.60 (t, 4H, CH$_2$), 1.60 (m, 4H, CH$_2$), 1.30 (m, 8H, CH$_2$). IR (NaCl, cm$^{-1}$): 1795, 1725 (C=O, anhydride), 1765 (C=O, ester). M$_w$=88800, PDI=1.3. T$_d$=325° C., T$_g$=37° C. Contact Angle: 71°.

Poly[1,6-bis(3,5-dimethoxy-1,4-carboxyphenoxy)-hexanoate] (1c). Yield: quantitative (white solid). $^1$H NMR (DMSO-d$_6$): δ 7.45 (s, 4H, ArH), 3.85 (s, 12H, CH$_3$), 2.65 (t, 4H, CH$_2$), 1.80 (t, 4H, CH$_2$). IR (NaCl, cm$^{-1}$): 1795, 1720 (C=O, anhydride), 1765 (C=O, ester). M$_w$=12500, PDI=2.0. T$_d$=289° C., T$_g$=86° C. Contact Angle: 60°.

Poly[1,10-bis(3,5-dimethoxy-1,4-carboxyphenoxy)-decanoate] (1d). Yield: quantitative (white solid). $^1$H NMR (DMSO-d$_6$): δ 7.45 (s, 4H, ArH), 3.80 (s, 12H, CH$_3$), 2.60 (t, 4H, CH$_2$), 1.65 (m, 4H, CH$_2$), 1.35 (m, 8H, CH$_2$). IR (NaCl, cm$^{-1}$): 1790, 1725 (C=O, anhydride), 1765 (C=O, ester). M$_w$=34300, PDI=1.9. T$_d$=335° C., T$_g$=79° C. Contact Angle: 75°.

Figure 4:
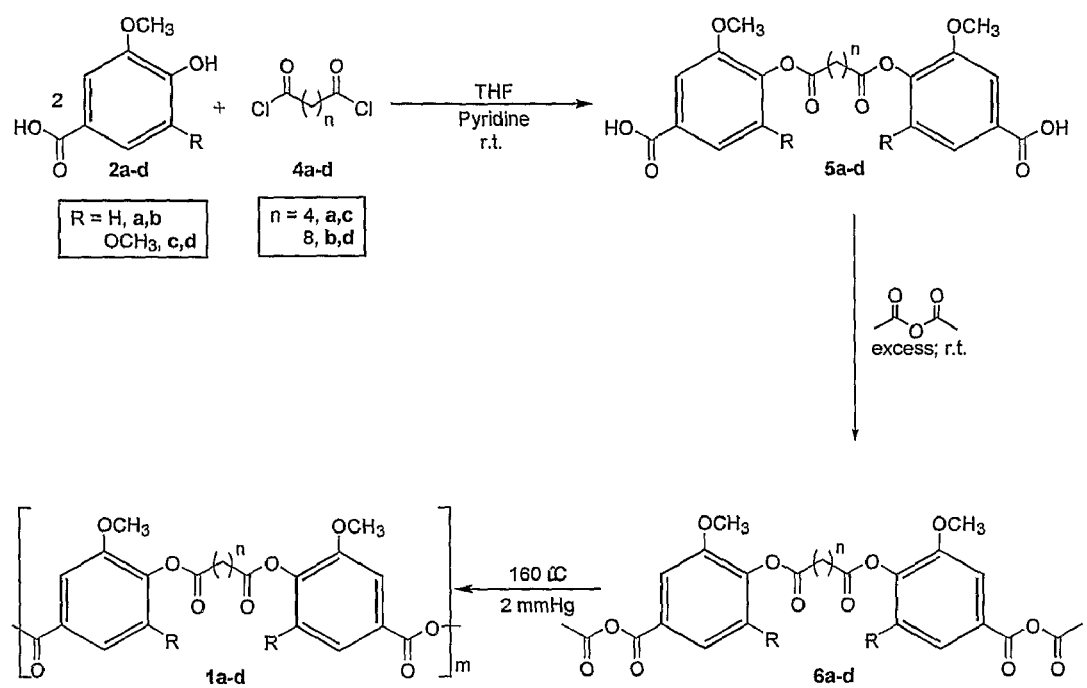
FIG. 4. Illustrates a synthetic scheme for preparing phenolic derivative-based poly(anhydride-esters), 1.

Poly(anhydride-esters) comprised of two phenolic derivatives (1) were prepared by melt-condensation polymerization methods as outlined in FIG. 4.

Polymer precursors or diacids (5) were synthesized according to previously described methods in yields ranging from 67 to 78% (see Uhrich, K. E. *Macromolecules* 2005, 38, 6895-6901; Schmeltzer, R., et al., *Polym. Bull.* 2003, 49, 441-448; and Fan, J., et al., *J Applied Polymer Science* 2006, 100, 1214-1221). Diacids (5) were activated into the monomers (6) with acetic anhydride and ultimately melt-polymerized at 160° C. under vacuum (<2 mmHg). The polymerization temperature was chosen based on the monomer decomposition temperature and polymerization time (4 h) upon solidification of the melt. The chemical incorporation of vanillic acid (VA) and syringic acid (SGA) into the polymeric backbone allowed a loading efficiency ranging from 67 up to 78 wt % (Table 1).

The polymers had molecular weights of 12,500-88,800, with the higher methoxy-substituted phenolic derivative-based polymers (1c,d) yielding the lowest molecular weights as shown in Table 1. Molecular weights significantly increased with the alkyl chain length of the compound linking the two phenolic derivative units. Similarly, alkyl linker chain length influenced polymer thermal properties, increasing decomposition temperature (T$_d$) and glass transition temperature (T$_g$) with the number of methylenes as previously demonstrated (see Prudencio, A.; Schmeltzer, R.; Uhrich, K. *Macromolecules* 2005, 38, 6895-6901). Glass transition temperatures (T$_g$) increased with the number of methoxy groups in the aromatic ring due to the decreased flexibility of the polymer chains. This trend of methoxy substitution on aromatic rings increasing the glass transition temperature (T$_g$) by a chain stiffening effect has been observed in polyesters containing methoxy-substituted aromatic rings.

TABLE 1

Properties of phenolic derivative-based poly(anhydride-esters) 1a-d.

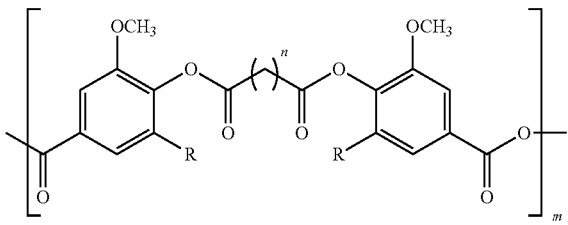

| Polymer | R | n | Cmpd. (%) | Contact Angle (°) | $T_g$ (°C.) | $T_d$ (°C.) | Molecular Weight |
|---|---|---|---|---|---|---|---|
| 1a | H, vanillic acid | 4 | 75.3 | 60 | 59 | 268 | 63100 |
| 1b | H, vanillic acid | 8 | 66.9 | 71 | 37 | 325 | 88800 |
| 1c | $OCH_3$, syringic acid | 4 | 78.3 | 60 | 86 | 289 | 12500 |
| 1d | $OCH_3$, syringic acid | 8 | 70.5 | 75 | 79 | 335 | 34300 |

Example 2

Degradation Studies

Sample preparation. Polymer pellets were prepared by pressing ground polymers (~150±5 mg) into 13 mm diameter×1 mm thick disks in an IR pellet die (International Crystal Laboratories, Garfield, N.J.) with a bench-top hydraulic press (Carver model M, Wabash, Ind.]. A pressure of 5,000 psi was applied for 5 min at room temperature. No change in polymer color was observed upon applying pressure.

Degradation media preparation. Degradation media consisted of phosphate buffer solution (PBS) containing 0.1 M potassium hydrogen phosphate and 0.1 M potassium dihydrogen phosphate. The pH was adjusted to 7.4 with 1 M sodium hydroxide and/or 1 N hydrochloric acid solutions and pH-measurements were performed on an Accumet® AR15 pH-meter (Fisher Scientific, Fair Lawn, N.J.).

In vitro hydrolytic degradation. Hydrolytic degradation of the polymers was performed by placing the disks in 20 mL Wheaton glass scintillation vials (Fisher, Fair Lawn, N.J.) with 10 mL of PBS, and incubating them at 37° C. with agitation using a controlled environment incubator-shaker (New Brunswick Scientific Co., Edison, N.J.) at 60 rpm for 8 days. The buffer solution was replaced by fresh solution (10 mL) after 2, 4, 8, and 24 h of incubation and then every 24 h. The spent media was analyzed by HPLC to determine the concentration of free vanillic acid (VA) and syringic acid (SGA) in solution at each time point and by UV to follow polymer degradation. Data (average of 3 samples per time point) were plotted into cumulative percent-time curves.

Free biologically active compound determination. Vanillic acid (VA) and syringic acid (SGA) contents in the degradation media were determined chromatographically by a Perkin-Elmer HPLC system consisting of a Series 200 quaternary LC pump, and an ISS 200 autosampler, on a Zorbax C-8 reverse-phase column (4.6×150 mm) at 25° C. using a mixture of methanol:DDW:TFA 50:49.05:0.05 v/v/v as mobile phase at a flow rate of 1.0 mL/min. A 785A absorbance detector set at 251 nm was used to detect vanillic acid (VA) and at 261 nm to detect syringic acid (SGA). A Dell OptiPlex GX110 computer running Perkin-Elmer TurboChrom 4 software was used for data collection and processing, and to automate the analysis via Perkin-Elmer Nelson 900 Series Interface and 600 Series Link. Free phenolic compound concentration in the degradation media was determined from standard curves generated with solutions of known concentrations ($2.5 \times 10^{-4}$–$1.1 \times 10^{-1}$ mg/mL). Degradation media was filtered through 0.45 µm poly(tetrafluoroethylene) (PTFE) syringe filters (Whatman, Clifton, N.J.) before elution.

Polymer degradation. UV spectroscopy ($\lambda$=251 and 261 nm, for VA and SGA, respectively) with a DU 520 UV/vis spectrophotometer (Beckman Instruments, Fullerton, Calif.) was used to follow polymer degradation by measuring phenolic compound concentration in any form of degradation product. UV data were calibrated against vanillic acid and syringic acid solutions of known concentrations ($5.7 \times 10^{-4}$–$1.2 \times 10^{-1}$ mg/mL).

Figure 1:
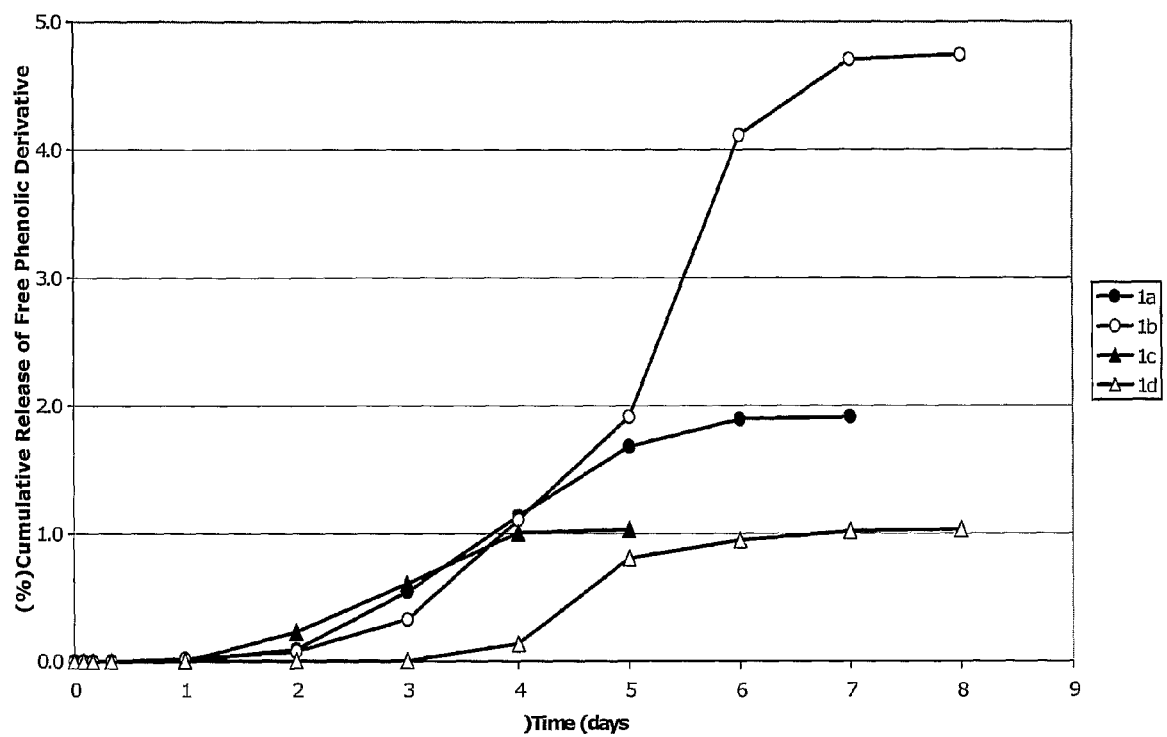
FIG. 1. Free phenolic derivative release from poly(anhydride-esters) 1a-d during hydrolytic degradation FIG. 2. Phenolic derivative-based poly(anhydride-esters) 1a-d hydrolytic degradation.

Polymer Hydrolytic Degradation. The hydrolytic degradation of phenolic derivative-based poly(anhydride-esters) was investigated on polymer disks immersed in pH 7.4 phosphate buffered solution at 37° C. for 5-8 days. Free phenolic derivative concentration in the degradation media at each time point was determined by HPLC and polymer degradation was followed by UV spectrometry. For polymer degradation to occur, water must penetrate into the matrix. Once water has penetrated into the matrix, anhydride and ester bonds are broken and solubilization of the degradation products becomes another critical step in the degradation/hydrolysis. The hydrolytic degradation of phenolic derivative-based poly (anhydride-esters) (1) initially yielded small oligomers and the monomer precursor or diacid (5) upon cleavage of the anhydride bonds. The diacid (5) further breaks into the phenolic derivative (2) and a carboxylic acid (3) via ester bond cleavage as confirmed by HPLC. HPLC chromatograms The retention times were 2.8 min and 2.9 min for vanillic acid (VA) and syringic acid (SGA), respectively. Cumulative percent of VA and SGA released in their free form at each time point during the degradation are presented in FIG. 1. Over the 5-8 day degradation period, cumulative release of SGA and VA in their free form ranged from 1.0-4.7%. The rest was accounted for vanillic acid and syringic acid in the form of diacid and/or small oligomers. The solubilities of the degradation products explain the amount of phenolic derivative in its free form detected in solution at each time point (FIG. 1). Based on the solubilities of vanillic acid (47 mg/mL) and syringic acid (56 mg/mL) in PBS, diacids and oligomers based on syringic acid are more soluble in the degradation media (PBS) than their analogues based on vanillic acid. The higher the solubility of the degradation products (oligomers and diacids), the more of these compounds will go in solution before breaking down into free phenolic derivative, yielding a lower concentration of phenolic derivative detected in solution. The polymers based on vanillic acid 1a and 1b released the higher amounts of phenolic derivative in solution, 1.9% and 4.7%, respectively, due to the lower solubility of the polymer degradation products as compared to those based on syringic acid. The lower amounts of free syringic acid detected in solution from the polymers 1c-d degradation is explained by the higher solubility of the corresponding diacids and/or small oligomers. decreased as the solubility of the other degradation products (diacids and small oligomers) increased.

Figure 2:
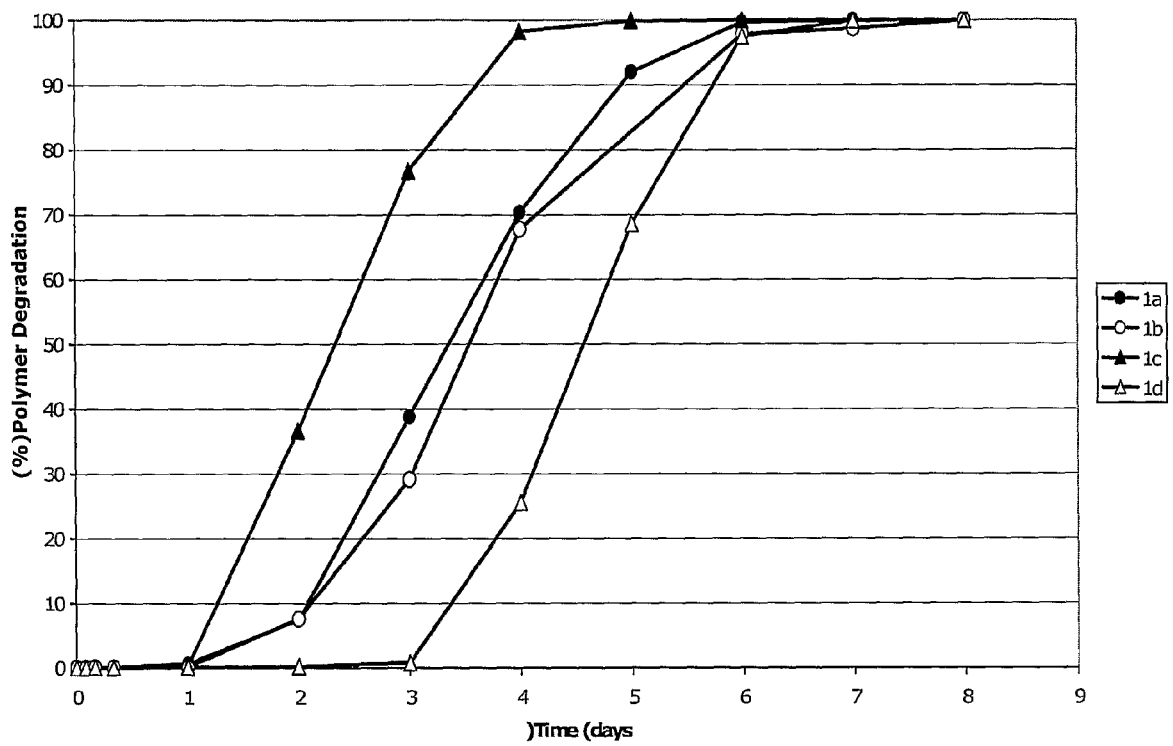

Polymer hydrophobicity/hydrophilicity is a good indicator of in vitro degradation rate as a factor that influences water penetration into the polymer matrix. Static contact angles of phosphate buffer solution (PBS) on the polymer disks surfaces ranging from 60 to 75° were measured to determine polymer hydrophobicity (Table 1). Polymer degradation rates were determined by UV measurements (FIG. 2) and decreased with higher contact angles (more hydrophobic). Indeed, polymer 1d displayed the highest contact angle value (75°) and also displayed the slowest degradation relative to the other poly(anhydride-esters) (1a-c). For the polymers 1a and 1c that had the same contact angles, the faster degradation rate of 1a is explained by the faster solubilization of the polymer degradation products. Polymer degradation rates (FIG. 2), determined by UV measurements, correlated with the solubility of vanillic (47 mg/mL) and syringic acid (56 mg/mL) in the degradation media (PBS) and contact angles. Polymers with the lowest contact angles were the fastest degrading, increasing with higher solubility. The amount of phenolic derivative in its free form detected in solution at each time point (FIG. 1) decreased as the solubility of the other degradation products (diacids and small oligomers) increased. Polymer degradation rates (FIG. 1), determined by HPLC measurements, correlated with the solubility of vanillic (47 mg/mL) and syringic acid (56 mg/mL) in the degradation media (PBS).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition suitable for topical administration to an animal comprising a polyanhydride homopolymer having a backbone that degrades within 60 hours of administration to provide a biologically active compound, wherein the biologically active compound is p-coumaric acid, ferulic acid, or sinapic acid.

2. The composition of claim 1 wherein the polyanhydride degrades within 18 hours of administration.

3. The composition of claim 1, wherein the biologically active compound is p-coumaric acid.

4. The composition of claim 1, wherein the biologically active compound is ferulic acid.

5. The composition of claim 1, wherein the biologically active compound is sinapic acid.

6. A composition suitable for topical administration comprising microspheres that degrade within 60 hours of administration, the microspheres comprising a polyanhydride homopolymer having a backbone that comprises one or more groups that will provide p-coumaric acid, ferulic acid, or sinapic acid upon hydrolysis of the backbone.

7. The composition of claim 6 wherein the microspheres degrade within 24 hours of administration.

8. The composition of claim 6, wherein the backbone comprises one or more groups that will provide p-coumaric acid upon hydrolysis of the backbone.

9. The composition of claim 6, wherein the backbone comprises one or more groups that will provide ferulic acid upon hydrolysis of the backbone.

10. The composition of claim 6, wherein the backbone comprises one or more groups that will provide sinapic acid upon hydrolysis of the backbone.

11. A composition suitable for topical administration to an animal comprising a polyanhydride homopolymer having a backbone that degrades within 60 hours of administration to provide a biologically active compound, wherein the polyanhydride comprises one or more units of the following formula:

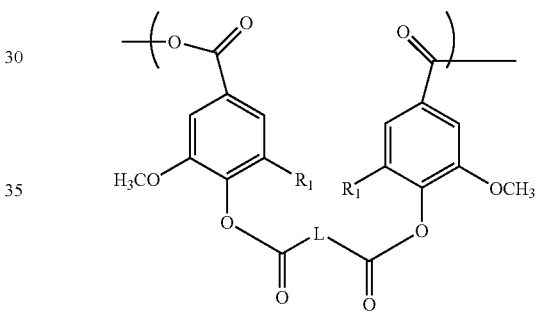

wherein:

each $R_1$ is independently H, or methoxy; and

L is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, hydroxy, oxo, carboxy, aryl, aryloxy, heteroaryl, and heteroaryloxy.

12. The composition of claim 11 wherein L is a divalent, branched or unbranched, saturated or unsaturated, hydrocarbon chain, having from 3 to 15 carbon atoms.

13. The composition of claim 11 wherein L is a divalent, branched or unbranched, hydrocarbon chain, having from 4 to 8 carbon atoms.

14. The composition of claim 11 wherein L is —$CH_2CH_2CH_2CH_2$—.

15. The composition of claim 11 wherein each $R_1$ is H.

16. The composition of claim 11 wherein each $R_1$ is methoxy.

17. A polyanhydride homopolymer that comprises units of the following formula (I):

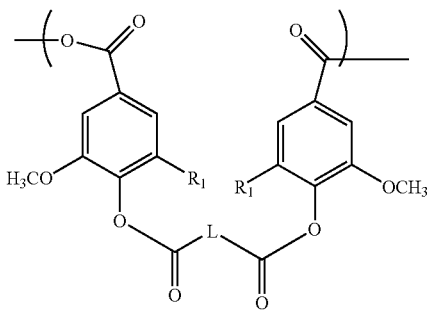

wherein:
each $R_1$ is independently H, or methoxy; and
L is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

18. The polyanhydride of claim 17 wherein L is a divalent, branched or unbranched, saturated or unsaturated, hydrocarbon chain, having from 3 to 15 carbon atoms.

19. The polyanhydride of claim 17 wherein L is a divalent, branched or unbranched, hydrocarbon chain, having from 4 to 8 carbon atoms.

20. The polyanhydride of claim 17 wherein L is —$CH_2CH_2CH_2CH_2$—.

21. The polyanhydride of claim 17 wherein each $R_1$ is H.

22. The polyanhydride of claim 17 wherein each $R_1$ is methoxy.

23. A method for preparing a polyanhydride of formula (I):

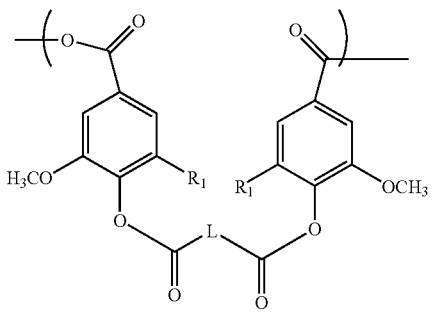

as described in claim 11 comprising polymerizing a corresponding compound of formula (II):

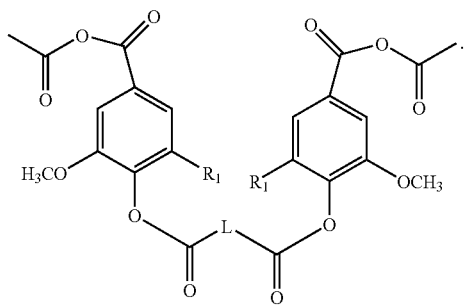

24. A composition suitable for topical administration to an animal comprising a polyanhydride homopolymer having a backbone that degrades within 60 hours of administration to provide a biologically active compound, wherein the polyanhydride comprises one or more units of the following formula:

wherein:
each $R_1$ is independently H, or methoxy; and
L is —$CH_2CH_2CH_2CH_2$—.

25. A method for promoting an antioxidant, antiseptic, or antibacterial effect comprising topically administering the composition of claims 1, 6 or 11 to an animal.

26. A method for administering a biologically active compound to an animal comprising topically applying to the animal a composition that comprises a polyanhydride homopolymer of claim 1 or 11.

27. The method of claim 26 wherein the polyanhydride degrades within 18 hours of administration.

* * * * *